United States Patent
Boulanger et al.

Patent Number: 5,489,697
Date of Patent: Feb. 6, 1996

[54] METHOD FOR THE PREPARATION OF (±)-CALANOLIDE A AND INTERMEDIATES THEREOF

[75] Inventors: William A. Boulanger, Schenectady, N.Y.; Michael T. Flavin, Darien, Ill.; Alla Kucherenko, Lemont, Ill.; Abram K. Sheynkman, Lemont, Ill.

[73] Assignee: MediChem Research, Inc., Lemont, Ill.

[21] Appl. No.: 285,655

[22] Filed: Aug. 3, 1994

[51] Int. Cl.$^6$ .................... C07D 311/78; C07D 311/76
[52] U.S. Cl. .................... 549/278; 549/282; 549/289
[58] Field of Search .................... 549/278, 282, 549/289

[56] References Cited

FOREIGN PATENT DOCUMENTS

WO94/14789  7/1994  WIPO.

OTHER PUBLICATIONS

Brookmeyer, R. (1991), *Science*, vol. 253, pp. 37–42.
Braun et al. (1990), *Annu. Rev. Microbiol.*, vol. 44, pp. 555–577.
Weislow et al. (1989), *J. Natl. Cancer Inst.*, vol. 81, 577–586.
Mitsuya et al. (1990), *Science*, vol. 249, pp. 1533–1544.
Petteway et al. (1991), *Trends Pharmacol. Sci.*, vol. 12, pp. 28–34.
Richman, D. D. (1991), *Annu. Rev. Med.*, vol. 42, pp. 69–90.
Hadden, J. W. (1991), *Trends Pharmacol. Sci.*, vol. 12, pp. 107–111.
Huff, J. R. (1991), *J. Med. Chem.*, vol. 34, pp. 2305–2314.
De Clercq, E. (1992), *AIDS Research and Human Retroviruses*, vol. 8, pp. 119–134.
Kashman et al. (1992), *J. Med. Chem.*, vol. 35, pp. 2735–2743.
Chenera et al. (1993), *J. Org. Chem.*, vol. 58, pp. 5605–5606.
Sethna et al. (1953), *Organic Reactions*, Chapter 1, pp. 1–58.
Crombie et al. (1987), *Chem. Soc.*, vol. 1, pp. 317–330.
Barton et al. (1990), *Tetrahedron Letters*, vol. 31, pp. 7449–7452.
Széll et al. (1969), *Helvetica Chimica Acta*, vol. 52, pp. 2636–2641.
Fung et al. (1978), *J. Org. Chem.*, vol. 43, pp. 3977–3979.
Gemal et al. (1981), *J. Am. Chem. Soc.*, vol. 103, pp. 5454–5459.
Rod, A. V. R. et al *Tetraheron Lett* (1994), 35(34), 6347–50.
Chenera, B. et al *J. Org. Chem* (1993), 58(21) 5605–6.

*Primary Examiner*—C. Warren Ivy
*Assistant Examiner*—Amelia Owens
*Attorney, Agent, or Firm*—Banner & Allegretti, Ltd.

[57] ABSTRACT

A method for preparing (±)-calanolide A, 1, a potent HIV reverse transcriptase inhibitor, from chromene 4 is provided. Useful intermediates for preparing (±)-calanolide A and its derivatives are also provided.

According to the disclosed method, chromene 4 intermediate was reacted with acetaldehyde diethyl acetal in the presence of an acid catalyst with heating to produce chromanone 7. Reduction of chromene 7 with sodium borohydride, in the presence of cerium trichloride, produced (±)-calanolide A, which was purified chromatographically.

7 Claims, No Drawings

METHOD FOR THE PREPARATION OF (+)-CALANOLIDE A AND INTERMEDIATES THEREOF

This invention was made with support from the U.S. Government under Grant No. 2R44AI34805 from the National Institutes of Health. The Government has certain rights in this invention.

FIELD OFF THE INVENTION

This invention relates to a method for the preparation of (±)-calanolide A, a potent inhibitor of HIV reverse transcriptase, and intermediates thereof.

BACKGROUND OF THE INVENTION

Human immunodeficiency virus (HIV), which is also called human T-lymphotropic virus type III (HTLV-III), lymphadenopathy-associated virus (LAV)or AIDS-associated retrovirus (ARV), was first isolated in 1982 and has been identified as the etiologic agent of the acquired immunodeficiency syndrome (AIDS) and related diseases. Since then, chemotherapy of AIDS has been one of the most challenging scientific endeavors. So far, AZT, ddC, ddI, and D4T have been approved by FDA and are being clinically used as drugs for the treatment of AIDS and AIDS-related complex. Although these FDA-approved drugs can extend the life of AIDS patients and improve their quality of life, none of these drugs are capable of curing the disease. Bone-marrow toxicity and other side effects as well as the emergence of drug-resistant viral strains limit the long-term use of these agents.[1] On the other hand, the number of AIDS patients worldwide has increased dramatically within the past decade and estimates of the reported cases in the very near future also continue to rise dramatically. It is therefore apparent that there is a great need for other promising drugs having improved selectivity and activity to combat AIDS.[1] Several approaches including chemical synthesis, natural products screening, and biotechnology have been utilized to identify compounds targeting different stages of HIV replication for therapeutic intervention.[2] Very recently, the screening program at the National Cancer Institute has discovered a class of remarkably effective anti-HIV natural products, named calanolides, from the rainforest tree *Calophyllum lanigerum*, with calanolide A, 1, being the most potent compound in the reported series.[3] For example, calanolide A demonstrated 100% protection against the cytopathic effects of HIV-1, one of two distinct types of HIV, down to a concentration of 0.1 µM. This agent also halted HIV-1 replication in human T-lymphoblastic cells (CEM-SS) ($EC_{50}$=0.1 µM/$IC_{50}$=20 µM).[3] More interestingly and importantly, calanolide A was found to be active against both the AZT-resistant G-9106 strain of HIV as well as the pyridinone-resistant A17 virus.[3] Thus, the calanolides, known as HIV-1 specific reverse transcriptase inhibitors, represent novel anti-HIV chemotherapeutic agents for drug development.

The only known natural source of calanolide A was destroyed and other members of the same species did not contain the desired material.[4] Consequently, a practical synthesis of the natural product must be developed for further study and development to be carried out on this active and promising series of compounds. Herein, we describe a method for the synthesis of (±)-calanolide A and some related compounds.

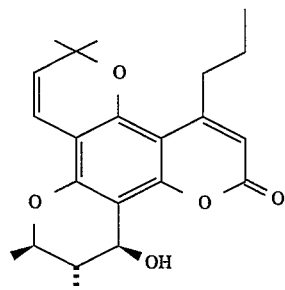

The key intermediate in the inventive method of preparation is chromene 4, which is synthesized by the sequence depicted in Scheme I. Thus, 5,7-dihydroxy-4-propylcoumarin, 2,[5] was prepared quantitatively from ethyl butyrylacetate and phloroglucinol under Pechman conditions.[6] Product yield and purity was dependent on the amount of sulfuric acid used. The 8-position of 5,7-dihydroxy-4-propylcoumarin, 2, was then selectively acylated at 8°–10° C. by propionyl chloride and $AlCl_3$ in a mixture of carbon disulfide and nitrobenzene to afford 5,7-dihydroxy-8-propionyl-4-propylcoumarin, 3. A route developed for synthesis of *Mammea coumarins*[7] was initially attempted for preparation of compound 3, but it proved too awkward and low-yielding. The chromene ring was introduced upon treatment of compound 3 with 4,4-dimethoxy-2-methylbutan-2-ol,[8] providing 4 in 78% yield.

Scheme I

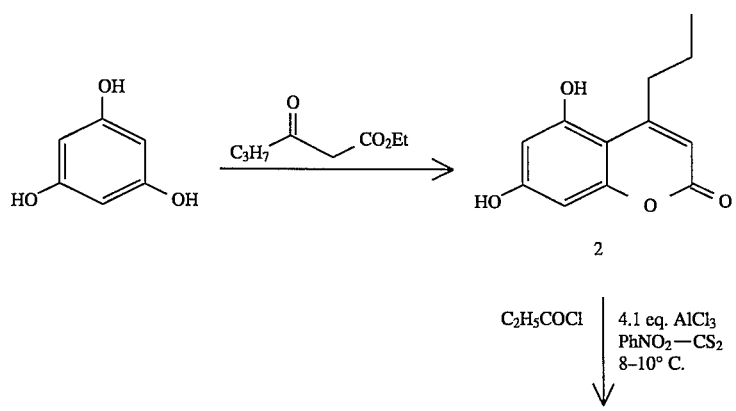

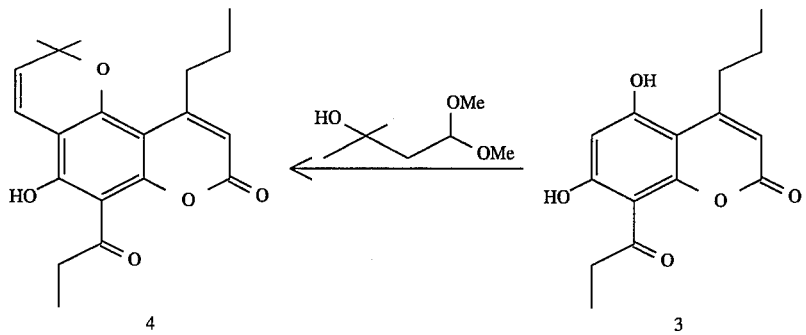

As presented in Scheme II, Robinson-Kostanecki reaction[9] on 4 by using sodium acetate in refluxing acetic anhydride produced enone 5 in a 65% yield. This intermediate failed to afford calanolide A upon reduction with borohydride reagents, presumably because attack at the pyrone and ring opening occurred preferentially. Treatment of 5 with Baker's yeast also resulted in coumarin ring cleavage while tri-n-butyltin hydride[10] led to reduction of 5 to enol 6 in modest yield. Finally, (±)-calanolide A was successfully formed with the desired stereochemical arrangement by treatment of 4 with acetaldehyde diethyl acetal in the presence of trifluoroacetic acid and pyridine with heating at 160° C., followed by Luche reduction[11] via chromanone 7 (see Scheme II).

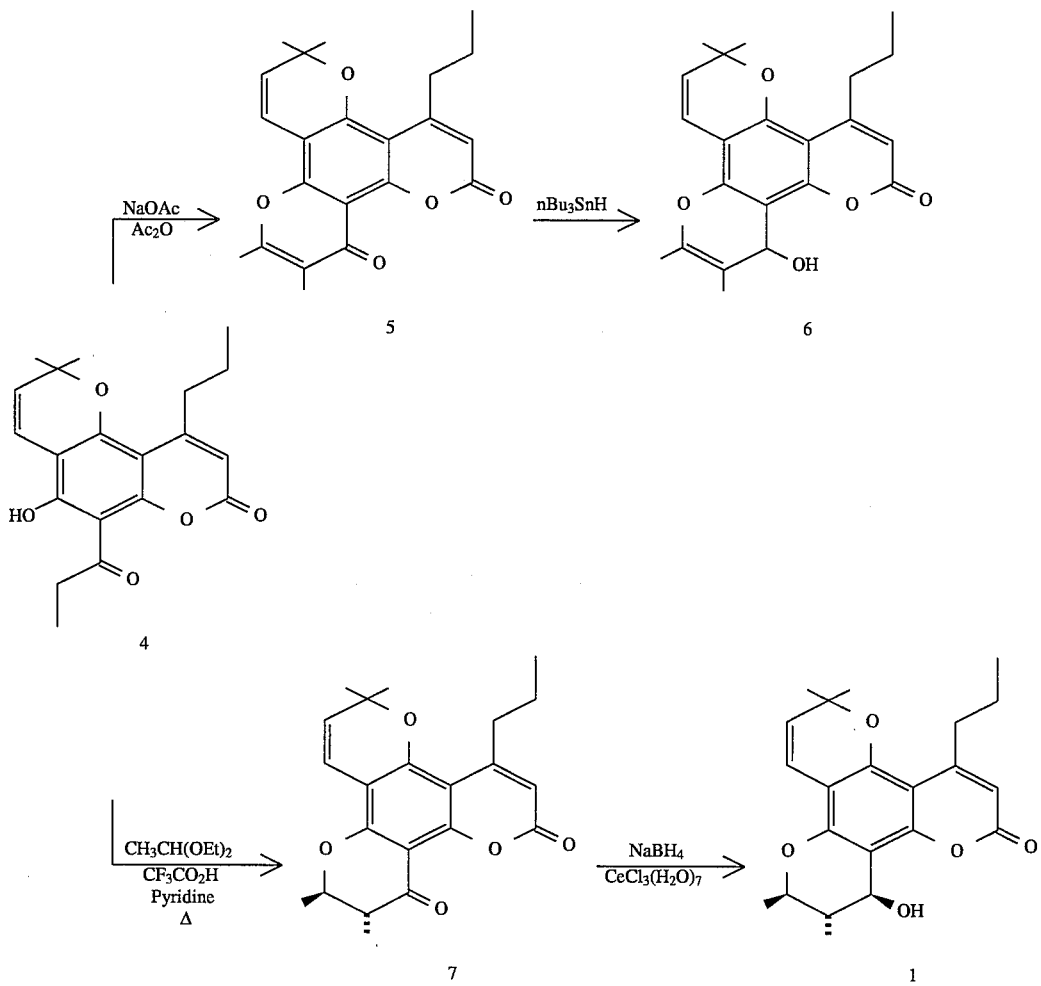

OBJECTS OF THE INVENTION

Accordingly, one object of the present invention is to provide a simple and practical method for preparing (±)-calanolide A, 1, from readily available starting materials.

Another object of the invention is to provide useful intermediates for preparing derivatives of (±)-calanolide A.

A further object of the invention is to provide a simple and practical method for preparing (±)-calanolide A in high yields from key intermediate chromene 4.

These and other objects of the invention will become apparent in view of the detailed description below.

DETAILED DESCRIPTION OF THE INVENTION

All chemical reagents and solvents referred to herein are readily available from a number of commercial sources including Aldrich Chemical Co. or Fischer Scientific. NMR spectra were run on a Hitachi 60 MHz R-1200 NMR spectrometer or a Varian VX-300 NMR spectrometer. IR spectra were obtained using a Midac M series FT-IR instrument. Mass spectral data were obtained using a Finnegan MAT 90 mass spectrometer. All melting points are corrected.

According to the method of the present invention, chromene 4 is a key intermediate in the preparation of (+)-calanolide A, 1. A preferred method for synthesizing chromene 4 from 5,7-dihydroxy-4-propylcoumarin, 2, is shown in Scheme I. According to this synthetic scheme, 5,7-dihydroxy-4-propylcoumarin, 2,[5] was prepared quantitatively from ethyl butyrylacetate and phloroglucinol under Pechman conditions.[6]

In conducting this reaction, a volume of a concentrated acid is added in a dropwise manner to a stirring mixture of ethyl butyrylacetate and phloroglucinol with a mole ratio ranging between about 3:1 and about 1:3, with a preferable range being about 0.9: 1.0. The dropwise addition of an acid was conducted at a rate such that the temperature of the reaction mixture is maintained at a temperature ranging between about 0° C. and about 120° C., preferably about 90° C.

Suitable, but not limiting, examples of concentrated acid include sulfuric acid, trifluoroacetic acid, and methanesulfonic acid. In practicing this invention, concentrated sulfuric acid is particularly preferred. As the product yield and purity appears to be dependent on the amount of concentrated sulfuric acid used, it is preferred that the amount of concentrated sulfuric acid range between about 0.5 and 10 mole, most preferably ranging between about 2 and about 3.5 mole, per mole of ethyl butyrylacetate.

The reaction mixture is then heated to a temperature ranging between about 40° C. and about 150° C., preferably about 90° C., until the reaction reaches completion as determined by TLC analysis. The reaction mixture is then poured onto ice and the precipitated product is collected by filtration and dissolved in an organic solvent. Suitable, but non-limiting, examples of organic solvents include ethyl acetate, chloroform, and tetrahydrofuran. A preferred solvent is ethyl acetate. The resulting solution is then washed with brine and dried over a suitable drying agent, e.g., sodium sulfate. The yields of this reaction are generally quantitative.

Thereafter, 5,7-dihydroxy-8-propionyl-4-propylcoumarin, 3, was prepared by selectively acylating the 8-position of 5,7-dihydroxy-4-propylcoumarin, 2, with propionyl chloride in the presence of a Lewis acid catalyst. In conducting this reaction, a solution of propionyl chloride in a suitable solvent, e.g., carbon disulfide, was added in a dropwise manner to a vigorously stirred solution of 5,7-dihydroxy-4-propylcoumarin, 2, a Lewis acid and an organic solvent cooled in an ice bath. Dropwise addition of propionyl chloride is conducted such that the temperature of the reaction mixture is maintained at a temperature ranging between 0° C., and about 30° C., preferably between about 8° C. and 10° C.

In practicing the invention, the amount of propionyl chloride used generally ranges between about 0.5 moles and about 6 moles, preferably ranging between about 1 mole and about 2 moles, per mole of 5,7-dihydroxy-4-propylcoumarin, 2.

Non-limiting examples of Lewis acid catalysts useful in the acylation reaction include $AlCl_3$, $SnCl_4$, $ZnCl_2$ and $TiCl_4$. A preferred Lewis acid catalyst is $AlCl_3$. The amount of Lewis acid catalyst relative to 5,7-dihydroxy-4-propylcoumarin, 2, ranges between about 0.5 and about 12 moles, preferably ranging between about 2 and about 5 moles, per mole of 5,7-dihydroxy-4-propylcoumarin, 2.

Non-limiting examples of organic solvent for use in preparing the 5,7-dihydroxy-4-propylcoumarin, 2, solution include nitrobenzene or toluene and mixtures thereof. A preferred organic solvent for use in this invention is nitrobenzene.

Upon completion of the addition of propionyl chloride, the vigorously stirred reaction mixture is maintained at a temperature ranging between about 0° C. and about 120° C., preferably ranging between about 25° C. and 80° C., until the reaction reaches completion as monitored by conventional means such as TLC analysis. The reaction mixture is then poured onto ice and extracted several times with a suitable solvent such as ethyl acetate, chloroform, methylene chloride, tetrahydrofuran, or a mixture of chloroform/methanol. A preferred solvent for this extraction is ethyl acetate. The extracts are then dried over a suitable drying agent, e.g., sodium sulfate, and the product may be purified by conventional means such as silica gel column chromatography.

The yields of 5,7-dihydroxy-8-propionyl-4-propylcoumarin, 3, produced by the above described reaction are generally quantitative. A route developed for the synthesis of *Mammea coumarins* was initially attempted for the preparation of compound 3, but it proved too awkward and low-yielding.[7]

Thereafter, chromene 4 was prepared by introducing the chromene ring into 5,7-dihydroxy-8-propionyl- 4-propylcoumarin, 3, using 4,4-dimethoxy-2-methylbutan-2-ol. According to the method of the present invention, a solution of 5,7-dihydroxy-8-propionyl-4-propylcoumarin, 3, and 4,4-dimethoxy-2-methylbutan-2-ol in a suitable organic solvent was reacted at a temperature ranging between about 40° C. and about 180° C., preferably ranging between about 100° C. and about 120° C., until the reaction reached completion as determined by conventional means such as TLC analysis.

In practicing this invention, the amount of 4,4-dimethoxy-2-methylbutan-2-ol employed in the reaction generally ranges between about 0.5 and about 8 moles, preferably ranging between about 2 and about 4 moles, per mole of 5,7-dihydroxy-8-propionyl-4-propylcoumarin, 3. Suitable, but non-limiting examples of organic solvents include pyridine, N,N-diethylaniline, and triethylamine. A preferred solvent for use in this invention is pyridine.

Upon completion of the reaction, the solvent is removed under reduced pressure and the reaction product is dissolved in a suitable solvent, e.g., ethyl acetate. The solution is then washed sequentially with water and brine and dried over a suitable drying agent, e.g., sodium sulfate. Thereafter, the crude chromene 4 product can be purified by conventional means such as silica gel column chromatography using 25% ethyl acetate/hexane as the elution solvent. The yields of chromene 4 generally fall within the range of about 60% and about 85%, usually resulting in about 78% yield.

Thereafter, chromanone 7 may be produced by reacting a solution of chromene 4, acetaldehyde diethylacetal, and an acid catalyst in organic solvent at a temperature ranging between about 60° C. and about 140° C., preferably about 140° C., until the reaction is completed.

The amount of acetaldehyde diethylacetal used in the reaction generally ranges between about 0.5 and about 10 moles, preferably ranging between about 3 and about 5 moles, per mole of chromene 4.

Suitable, but non-limiting, examples of acid catalysts include pyridinium toslylate, trifluoroacetic acid, methanesulfonic acid, acetic acid, pyridinium hydrofluoride, pyridinium trifluoroacetate, and mixtures thereof. A preferred acid catalyst for the use in this invention is trifluoroacetic acid. The amount of acid catalyst used generally ranges between about 2 and about 25 moles, preferably ranging between about 17 and about 22 moles, per mole of chromene 4.

Finally, mild selective borohydride reduction of chromene 7 in the presence of $CeCl_3(H_2O)_7$ produced (±)-calanolide A with the desired stereochemical arrangement. In conducting the reduction reaction, a solution of chromene 7 was added dropwise into a solution of sodium borohydride and $CeCl_3(H_2O)_7$ in ethanol. The rate of addition is such that the reaction mixture temperature is maintained within a range of between about −40° C. and about 60° C., preferably ranging between about 10° C. and about 30° C. Thereafter, the reaction mixture was stirred at a temperature ranging between about −40° C. and about 60° C.

In general, the amount of $CeCl_3(H_2P)_7$ present in the reaction mixture ranged between about 0.1 and about 2 mole, preferably ranging between about 0.5 and about 1 mole, per mole of sodium borohydride. In addition, the amount of sodium borohydride employed in the reaction generally ranged between about 0.1 and about 12 mole, preferably ranging between about 2 and about 4 moles, per mole of chromanone 7. Suitable, but non-limiting, examples of reducing agents include $LiAlH_4$, $(i-Bu)_2AlH$, $(n-Bu)_3SnH$, 9-BBN, and enzymes such as baker yeast. Suitable, but non-limiting, examples of metal additives include $ZnCl_2$, $AlCl_3$, $TiCl_4$, $SnCl_3$, and $LnCl_3$.

Thereafter, the reduction mixture was diluted with water and extracted with a suitable solvent, e.g., ethyl acetate. The extract was dried over a suitable drying agent, e.g., sodium sulfate, and concentrated. The resulting residue was then purified by conventional means such as silica gel chromatography, using ethyl acetate/hexane solvent mixtures.

Thus, (±)-calanolide A, 1, was successfully prepared with the desired stereochemical arrangement by treatment of the key intermediate chromene 4 with acetaldehyde diethyl acetal in the presence of trifluoroacetic acid and pyridine to produce chromanone 7, followed by Luche reduction via chromanone 7 (see Scheme II). An alternative route for preparing (±)-calanolide A from chromene 4 was attempted. A Robinson-Kostanecki reaction on 4 was conducted with sodium acetate in refluxing acetic anhydride and produced enone 5 in a 65–70% yield (see Scheme II). Enone 5, however, failed to afford (±)-calanolide A when being reduced with borohydride reagents, presumably because attack at the pyrone and ring opening occurred preferentially. Treatment of compound 5 with Baker's yeast also resulted in coumarin ring cleavage while tri-n-butyltin hydride reduced enone 5 into enol 6 in a modest yield.

The following examples are illustrative and do not serve to limit the scope of the invention as claimed.

EXPERIMENTAL

NMR spectra were run either on a Hitachi 60 MHz R-1200 NMRspectrometer or a Varian VX-300 NMR spectrometer. LR spectra were obtained using a Midac M series FT-IR instrument. Mass spectra were obtained using a Finnegan MAT 90 mass spectrometer. All melting points are corrected.

5,7-Dihydroxy-4-Propyicoumarin (2):[5]

Concentrated sulfuric acid (200 mL) was added into a mixture of phloroglucinol dihydrate (150 g, 0.926 mol) and ethyl butyrylacetate (161 g, 1.02 mol). The resulting mixture was stirred at 90° C. for two hours whereupon it was poured onto ice. The solid product was collected by filtration, and then dissolved in ethyl acetate. The solution was washed with brine and dried over $Na_2SO_4$. After removal of the solvent in vacuo, the residue was triturated with hexane to provide essentially pure compound 2 (203 g) in quantitative yield, mp 233°–235° C. (Lit.[5] 236°–238° C.). $^1$H-NMR[5] (DMSO-$d_6$) δ 0.95 (3H, t, J=6.9 Hz, $CH_3$); 1.63 (2H, apparent hextet, J=7.0 Hz, $CH_2$); 2.89 (2H, t, J=7.5 Hz, $CH_2$); 5.85 (1H, s, $H_3$); 6.22 (1H, d, J= 2.0 Hz, $H_6$); 6.31 (1H, d, J=2.0 Hz, $H_8$); 10.27 (1H, s, OH); 10.58 (1H, s, OH); MS (EI): 220 (100, M+); 205 (37.9, M-$CH_3$); 192 (65.8, M-$C_2H_4$); 177 (24.8, M-$C_3H_7$); 164 (60.9, M-$CHCO_2$+1); 163 (59.6, M-$CHCO_2$); IR (KBr): 3210 (vs and broad, OH); 1649 (vs, sh); 1617 (vs, sh); 1554 (s) cm$^{-1}$; Anal. calc. for $C_{12}H_{24}O_4$: C, 65.45; H, 5.49; Found: C, 65.61; H, 5.44.

5,7-Dihydroxy-8-Propionyl-4-Propylcoumarin (3):

A three-neck flask (500 mL) equipped with an efficient mechanical stirrer, thermometer and addition funnel was charged with 5,7-dihydroxy-4-propylcoumafin, 2, (25.0 g, 0.113 tool), aluminum chloride (62.1 g; 0.466 tool), and nitrobenzene (150 mL) and the mixture was stirred until a solution was obtained, which was cooled to 0° C. in an ice bath. A solution of propionyl chloride (15.2 g; 0.165 mol) in carbon disulfide (50 mL) was added dropwise at such a rate that the reaction temperature was maintained at 8°–10° C. Addition was completed over a period of 1 hour with vigorous stirring. The reaction was monitored by TLC using a mobile phase of 50% ethyl acetate/hexane. After three hours, an additional portion of propionyl chloride (2.10 g; 0.0227 tool) in carbon disulfide (10 mL) was added. Immediately after the TLC analysis indicated the total consumption of starting material, the reaction mixture was poured onto ice, and allowed to stand overnight. The nitrobenzene was removed by steam distillation, and the remaining solution was extracted several times with ethyl acetate. The extracts were combined and dried over $Na_2SO_4$. The crude product obtained by evaporation in vacuo was purified by chromatography on a silica gel column eluting with 50% ether/hexane to provide the desired propionylated coumarin 3, mp (corr) 244°–246° C. $^1$H-NMR (DMSO-$d_6$) δ 0.96 (3H, t, J=7.3 Hz, $CH_3$); 1.10 (3H, t, J=7.2 Hz, $CH_3$); 1.60 (2H, m, $CH_2$); 2.88 (2H, t, J= 7.7 Hz, $CH_2$); 3.04 (2H, q, J=7.2 Hz, $CH_2$); 5.95 (1H, s, $H_3$); 6.31 (1H, s, $H_6$); 11.07 (1H, s, OH); 11.50 (1H, s, OH); MS (EI): 277 (6.6, M+1); 276

(9.0, M+); 247 (100, M-C$_2$H$_5$); IR (KBr): 3239 (s and broad, OH); 1693 (s, C=O), 1625 and 1593 (s) cm$^{-1}$; Anal. calc. for C$_{15}$H$_{16}$O$_5$: 65.21; H, 5.84; Found: C,64.92; H, 5.83. The isomer assignment was made by analogy to precedent.[7]

5-Hydroxy-2,2-Dimethyi-6-Propionyl-10-propyl-2H,8H-benzo[1,2-b:3,4-b']-dipyran- 8-one (4):

A mixture of 3 (2.60 g, 9.42 mmol) and 4,4-dimethoxy-2-methylbutan-2-ol (5.54 g, 37.7 retool) were dissolved in anhydrous pyridine (6.5 mL). The mixture was refluxed under nitrogen for three days. After removal of the solvent in vacuo, the residue was dissolved in ethyl acetate. The ethyl acetate was washed several times with 1N HCl and brine. It was then dried over Na$_2$SO$_4$. The crude product obtained by evaporation in vacuo was purified by silica gel column chromatography, eluting with 25% ethyl acetate/hexane to afford 2.55 g of 4 in 78.6% yield, mp 96°–98° C. $^1$H-NMR (CDCl$_3$) δ 1.05 (3H, t, J =7.3 Hz, CH$_3$); 1.22 (3H, t, J=7.5 Hz, CH$_3$); 1.53 (6H, s, 2 CH$_3$); 1.75 (2H, m, CH$_2$); 2.92 (2H, t, J=7.1 Hz, CH$_2$); 3.35 (2H, q, J= 7.1 Hz, CH$_2$); 5.56 (1H, d, J=10.0 Hz, H$_3$); 5.98 (1H, s, H$_9$); 6.72 (1H, d, J=10.0 Hz, H$_4$); MS (EI): 343 (5.7, M+1); 342 (22.5, M+); 327 (100, M-CH$_3$); IR (KBr): 1728 (vs, C=O) cm$^{-1}$; Anal. calc. for C$_{20}$H$_{22}$O$_5$: 70.16; H, 6.48; Found: C, 70.45; H, 6.92.

10,11-Didehydro-12-Oxocalanolide A or 6,6,10,11,-Tetramethyl-4-Propyl-2H,6H,12H-benzo[ 1,2-b:3,4-b':5,6-b"]tripyran-2,12-dione (5):

A mixture of 4 (1.76 g, 5.11 mmol) and sodium acetate (0.419 g, 5.11 mmol) in acetic anhydride (12 mL) were refluxed for 10 hours whereupon the solvent was removed in vacuo. The residue was purified by silica gel column chromatography, eluting first with 25% ethyl acetate/hexane followed by 50% ethyl acetate/hexane to provide 1.16 g of enone 5 (62% yield) as a white solid, mp 209°–209.5° C. $^1$H-NMR (CDCl$_3$) δ 1.05 (3H, t, J=6.6 Hz, CH$_3$); 1.56 (6H, s, 2 CH$_3$); 1.73 (2H, m, CH$_2$); 1.98 (3H, s, CH$_3$); 2.38 (3H, s, CH$_3$); 2.91 (2H, t, J=7.5 Hz, CH$_2$); 5.69 (1H, d, J=10.0 Hz, H$_7$); 6.11 (1H, s, H$_3$); 6.71 (1H, d, J=10 Hz, H$_8$); MS (EI): 366 (29.6, M+); 351 (100, M-CH$_3$); 323 (16.5, M-C$_3$H$_7$); IR (KBr): 1734 (vs, C=O), 1657, 1640, 1610, and 1562 cm$^{-1}$; Anal. calc. for C$_{22}$H$_{22}$2O$_5$: 72.12; H, 6.05; Found: C, 72.14; H, 6.15.

10,11-Didehydrocalanolide A or 12-Hydroxy-6,6,10,11-Tetramethyl-4-Propyl-2H,6H,12H-benzo[1,2-b:3,4-b':5,6-b"]tripyran-2-one (6):

A mixture of enone 5 (160 mg, 0.437 mmol) and tri-n-butyltin hydride (0.318 g, 1.09 mmol) in dry dioxane (2.0 mL) was refluxed under nitrogen for 12 hours. The solvent was then removed in vacuo and the residue was purified by preparative TLC using 25% ethyl acetate in hexane as the mobile phase. The product exhibited an R$_f$ of about 0.4. Enol 6 (13.3 rag, 8%) was isolated as an oil from the plate by ethyl acetate elution. This elution may have been inefficient, and the actual yield higher, as indicated by analytical TLC of the crude product. $^1$H-NMR (CDCl$_3$) δ 0.92 (3H, t, J=6.0 Hz, CH$_3$); 1.26 (3H, s, CH$_3$); 1.39 (3H, s, CH$_3$); 1.63 (2H, m, CH$_2$); 1.96 (3H, s, CH$_3$); 2.36 (3H, s, CH$_3$); 2.45 (2H, t, J=6.0 Hz, CH$_2$); 3.65 (1H, s, H$_{12}$); 5.51 (1H, d, J=10.0 Hz, H$_7$); 6.06 (1H, s, H$_3$); 6.67 (1H, d, J=10.0 Hz, H$_8$); 13.25 (1H, br s, OH); MS (EI): 369 (3.8, M+1), 368 (4.4, M+), 367 (8.3, M-1) 366 (28.4, M-2), 351 (100, M-OH); IR (KBr): 1651 (s), 1589 (m) cm$^{-1}$.

12-Oxocalanolide A or 10,11-Trans-Dihydro-6,6,10,11,-Tetramethyl-4-Propyl-2H,6H,12H-benzo[1,2-b:3,4-b':5,6-b"]Tripyran-2,12-Dione (7):

A solution containing chromene 4 (344 mg, 1.0 mmol), acetaldehyde diethylacetal (473 rag, 4.0 mmol), trifluoroacetic acid (1.5 mL, 19.4 mmol) and anhydrous pyridine (0.7 mL) was heated at 140° C. under N$_2$. The reaction was monitored by TLC analysis. After 4 hours, the reaction mixture was cooled to room temperature, diluted with ethyl acetate and washed several times with 10% aqueous NaHCO$_3$ and brine. The organic layer was separated and dried over Na$_2$SO$_4$. The solvent was removed in vacuo and the crude product was purified by silica gel column chromatography eluting with ethyl acetate/hexane (2:3). Chromanone 7 (110 rag, 30% yield) was obtained. $^1$H-NMR[5] (CDCl$_3$) δ 1.02 (3H, t, J=7.5 Hz, CH$_3$); 1.21 (3H, d, J=6.8 Hz, CH$_3$); 1.51 (3H, d, J=7.0 Hz, CH$_3$); 1.55 (6H, 2s, 2 CH$_3$); 1.63 (2H, sextet, J=7.0 Hz, CH$_2$); 2.55 (1H, dq, J= 6.9 Hz, J=11.0 Hz, H$_{11}$); 2.88 (2H, t, J=7.6 Hz, CH$_2$); 4.28 (1H, dq, J=6.3 Hz, J=11.0 Hz, H$_{10}$); 5.60 (1H, d, J=9.9 Hz, H$_8$); 6.04 (1H, s, H$_3$); 6.65 (1H, d, J=11.8 Hz, H$_7$); MS (CI): 369 ( 100, M+1).

(±)-Calanolide A (1):

To a solution ofchromanone 7 (11 mg, 0.03 mmol) in EtOH (0.4 mL) was added sodium borohydride (2.26 g, 0.06 mmol) and CeCl$_3$(H$_2$O)$_7$ (11.2 mg, 0.03 mmol) in EtOH (5 mL) at room temperature. After stirring for 45 minutes, the mixture was diluted with H$_2$O and extracted with ethyl acetate. The organic layer was dried over Na$_2$SO$_4$ and concentrated. The crude product was purified by preparative TLC eluting with ethyl acetate/hexane (1:1) to afford (±)-calanolide A (1) (10.5 rag, 94%). $^1$H-NMR[3] (CDCl$_3$) δ 1.04 (3H, t, J=7.4 Hz, CH$_3$); 1.15 (3H, d, J= 6.8 Hz, CH$_3$); 1.45 (6H, m, 2 CH$_3$); 1.51 (3H, s, CH$_3$); 1.65 (2H, m, CH$_2$); 1.95 (1H, m, H$_{11}$); 2.90 (2H, m, CH$_2$); 3.65 (1H, br s, OH); 3.92 (1H, m, H$_{10}$); 4.72 (1H, d, J= 7.7 Hz, H$_{12}$); 5.54 (1H, d, J=10.4 Hz, H$_7$); 5.95 (1H, s, H$_3$); 6.62 (1H, d, J=10.1 Hz, H$_8$); MS-CI: 371 (6.3, M+1); 370 (1.9, M+); 354 (24.6, M-OH+1); 353 (100, M-OH); 352 ( 15.8, M-H$_2$O); 339 (12.8, M-CHOH-1).

REFERENCES

1a. Brookmeyer, R., Reconstruction and Future Trends of the AIDS Epidemic in the United States. *Science*, 1991, 253, 37–42.

b. Brain, M. M.; Heyward, W. L.; Curran, J. W., The Global Epidemiology of HIV Infection and AIDS. *Annu. Rev. Microbial.*, 1990, 44, 555–577.

2a. Weislow, O.S.; Kiser, R.; Fine, D. L.; Bader, J.; Shoemaker, R. H.; Boyd, M. R., New Soluble-formazan Assay for HIV-1 Cytopathic Effects: Application to High-Flux Screening of Synthetic and Natural Products for AIDS-Antiviral Activity. *J. Natl. Cancer Inst.*, 1989, 81, 577–586.

b. Mitsuya, H.; Yarchoan, R.; Broder, S., Molecular Targets for AIDS Therapy. *Science*, 1990, 249, 1533–1544.

c. Petteway, S. R., Jr.; Lambert, D. M.; Metcalf, B. W., The Chronically Infected Cells: A Target for the Treatment of HIV Infection and AIDS. *Trends Pharmacol. Sci.*, 1991, 12, 28–34.

d. Richman, D. D., Antiviral Therapy of HIV Infection. *Annu. Rev. Med.*, 1991, 42, 69–90.

e. Haden, J. W., Immunotherapy of Human Immunodeficiency Virus Infection. *Trends Pharmacol Sci.*, 1991, 12, 107–111.

f. Huff, J. R., HIV Protease: A Novel Chemotherapeutic Target for AIDS. *J. Med Chem.*, 1991, 34, 2305–2314.

g. De Clercq, E., HIV Inhibitors Targeted at the Reverse Transcriptase. *AIDS Research and Human Retroviruses*, 1992, 8, 119–134.

3. Kashman, Y.; Gustafson, K. R.; Fuller, R. W.; Cardellina, J. H., II; McMahon, J. B.; Currens, M. J.; Buckheit, R. W., Jr; Hughes, S. H.; Cragg, G. M.; Boyd, M. R., The Calanolides, a Novel HIV-Inhibitory Class of Coumarin Derivatives from the Tropical Rainforest Tree, *Calophyllum lanigerum. J. Med. Chem.* 1992, 35, 2735–2743.

4. Boyd, M. R., National Cancer Institute, Personal Communication.

5. Chenera, B.; West, M. L.; Finklestein, J. A.; Dreyer, G. B., Total Synthesis of (±)-Calanolide A, a Non-Nucleoside Inhibitor of HIV-1 Reverse Transcriptase. *J. Org. Chem.* 1993, 58, 5605–5606.

6. Sethna, S.; Phadke, R., The Pechmann Reaction. *Organic Reactions*, 1953, 7, 1–58 and references cited therein.

7. Crombie, L.; Jones, R. C. F.; Palmer, C. J., Synthesis of the *Mammea Coumarins*. Part 1. The Coumarins of the Mammea A, B, and C Series. *J. Chem. Soc., Perkin Trans.* 1, 1987, 317–331.

8. Barton, D. H. R.; Donnelly, D. M. X; Finet, J. P.; Guiry, P. J., Total synthesis of Isorobustin. *Tetrahedron Lett.* 1990, 31, 7449–7452.

9. Kovacs, T. S.; Zarandy, M. S.; Erdohelyi, A., Cyclization of the Enol Esters of σ-Acyloxyphenyl Alkyl Ketones, IV. A Kinetic Study of the Steps of the Kostanecki-Robinson Reaction. *Helv. Chim. Acta*, 1969, 52, 2636–2641.

10. Fung, N. Y. M.; de Mayo, P.; Schauble, J. H.; Weedon, A. C., Reduction by Tributyltin Hydride of Carbonyl Compounds Adsorbed on Silica Gel: Selective Reduction of Aldehydes. *J. Org. Chem.* 1978, 43, 3977–3979.

11. Gemal, A, L.; Luche, J. L., Lanthanoids in Organic Synthesis. 6. The Reduction of α-Enones by Sodium Borohydride in the Presence of Lanthanoid Chlorides: Synthetic and Mechanistic Aspects. *J. Am. Chem. Soc.*, 1981, 103, 5454–5459.

What is claimed is:

1. A method for the preparation of (±)-calanoiide A comprising the steps of:

(a) condensing ethyl butyrylacetate and phloroglucinol in the presence of an acid catalyst to form 5,7-dihydroxy-4-propylcoumarin;

(b) acylating 5,7-dihydroxy-4-propylcoumarin with propionyl chloride in the presence of a Lewis acid to form 4-propyl-5,7-dihydroxy-8-propionylcoumarin;

(c) reacting 5,7-dihydroxy-8-propionyl-4-propylcoumarin with 4,4-dimethoxy-2-methylbutan-2-ol so as to produce 5-Hydroxy-2,2-dimethyl-6-propionyl- 10-propyl -2H,8H-benzo[1,2-b: 3,4-b']-dipyran-8one;

(d) reacting 5-Hydroxy-2,2-dimethyl-6-propionyl-10-propyl-2H,8H-benzo[ 1,2-b: 3,4-b']-dipyran-8 -one with acetaldehyde diethyl acetal in the presence of an acid catalyst to form 12-oxocalanolide A; and (e) reducing 12-oxocalanolide A so as to form (+)-calanolide A.

2. The method of claim 1, wherein the acid catalyst comprises sulfuric acid, trifluoroacetic acid, or methanesulfonic acid.

3. The method of claim 1, wherein step (e) is performed with a reducing agent comprising sodium borohydride in the presence of a metal additive comprising $CeCl_3(H_2O)_7$, $ZnCl_2$, $AlCl_3$, $TiCl_4$, $SnCl_3$, or $LnCl_3$.

4. The method of claim 1, wherein step (a) acid catalyst comprises sulfuric acid, trifluoroacetic acid, methaneslfonic acid, or trifluoromethanesulfonic acid.

5. The method of claim 1, wherein step (b) Lewis acid comprises $AlCl_3$, $ZnCl_2$, $TiCl_4$, or $SnCl_4$.

6. 5-Hydroxy-2,2-dimethyl-6-propionyl-10propyl-2H, 8H-benzo[1,2-b: 3,4-b']-dipyran-8-one.

7. 5,7-Dihydroxy-8-propionyl-4-propylcoumarin.

\* \* \* \* \*

UNITED STATES PATENT AND TRADEMARK OFFICE
CERTIFICATE OF CORRECTION

PATENT NO. : 5,489,697

DATED : February 6, 1996

INVENTOR(S) : W.A. Boulanger et al.

Page 1 of 4

It is certified that error appears in the above-indentified patent and that said Letters Patent is hereby corrected as shown below:

On the Title page, item [54], delete "( + )" and insert --( ± )--;

On the Title page, item [56], delete "Rod, A.V.R. et al. Tetraheron Lett (1994),, 35(34), 6347-50" and insert --Rod, A.V.R. et al. (1994), *Tetrahedron Lett.*, Vol. 35, pp. 6347-50;

On the Title page, item [56], delete "Chenera, B. et al. J. Org. Chem (1993), 58(21) 5605-6.";

On the Title Page, item [57], second paragraph, first line after "chromene" insert --,-- and after "4" insert --,--;

On the Title Page, item [57], second paragraph, fourth line, delete "chromene" and insert --chromanone--;

In Col. 1, line 1, delete "( + )" and insert --( ± )--;

In Col. 1, line 19, delete "(LAV)or" and insert --(LAV) or--;

In Col. 1, line 43, delete "anti-FIIV" and insert --anti-HIV--;

In Col. 2, line 35, delete "fin" and insert --rin--;

In Col. 2, line 36, delete "Pechman" and insert --Pechmann--;

In Col. 2, line 39, delete "fin" and insert --rin--;

In Col. 2, line 44, delete "*coumarins*" and insert --coumarins--;

In Col. 5, line 19, delete "Fischer" and insert --Fisher--;

In Col. 5, line 32, delete "Pechman" and insert --Pechmann--;

In Col. 5, line 50, delete first "mole," and insert --moles,--;

UNITED STATES PATENT AND TRADEMARK OFFICE
CERTIFICATE OF CORRECTION

PATENT NO. : 5,489,697

DATED : February 6, 1996

INVENTOR(S) : W.A. Boulanger et al.

It is certified that error appears in the above-indentified patent and that said Letters Patent is hereby corrected as shown below:

In Col. 6, line 43, delete "*coumarins*" and insert --coumarins--;

In Col. 7, line 26, delete "chromene" and insert --chromanone--;

In Col. 7, line 29, delete "chromene" and insert --chromanone--;

In Col. 7, line 37, delete "$CeCl_3(H_2P)$" and insert --$CeCl_3(H_2O)$--;

In Col. 7, line 39, delete "mole," and insert --moles,--;

In Col. 7, line 40, delete first "mole" and insert --moles,--;

In Col. 7, line 42, delete "mole," and insert --moles,--;

In Col. 7, line 46, delete "baker" and insert --Baker's--;

In Col. 8, line 12, delete "LR" and insert --IR--;

In Col. 8, line 17, delete "-Propyicoumarin" and insert --Propylcoumarin--;

In Col. 8, line 42, delete "-propylcoumafin" and insert --propylcoumarin--;

In Col. 8, line 43, delete first "tool" and insert --mol-- and delete second "tool" and insert --mol--;

In Col. 8, line 53, delete "tool" and insert --mol--;

In Col. 9, line 3, between "$O_6$:" and "65.21" insert -- C, --;

In Col. 9, line 6, delete "Dimethyi" insert --Dimethyl--;

In Col. 9, line 9, delete "retool" and insert --mmol--;

In Col. 9, line 24, between "$O_6$:" and "70.16" insert --C, --;

UNITED STATES PATENT AND TRADEMARK OFFICE
CERTIFICATE OF CORRECTION

PATENT NO. : 5,489,697

DATED : February 6, 1996

INVENTOR(S) : W.A. Boulanger et al.

It is certified that error appears in the above-indentified patent and that said Letters Patent is hereby corrected as shown below:

In Col. 9, line 44, delete "$H_{222}$" and insert --$H_{22}$-- and between "$O_6$:" and "72.12" insert --C, --;

In Col. 9, line 49, after "benzo" delete "[";

In Col. 9, line 50, before "1,2" insert --[--;

In Col. 10, line 20, delete "rag" and insert --mg--;

In Col. 10, line 32, delete "ofchromanone" and insert --of chromanone--;

In Col. 10, line 40, delete "rag" and insert --mg--;

In Col. 10, line 57, delete "*Microbial.*" and insert --*Microbiol.*--;

In Col. 11, line 30, delete first "*Coumarins*" and insert --Coumarins--;

In Col. 11, line 31, delete "Mammea" and insert --*Mammea*--;

In Col. 12, line 7, delete "calanoiide" and insert --calanolide--;

In Col. 12, line 15, delete "4-propyl-5,7-dihydroxy-8-propionylcoumarin" and insert --5,7-dihydroxy-8-propionyl-4-propyl-coumarin--;

In Col. 12, line 18, delete "Hydroxy" and insert --hydroxy--;

In Col. 12, line 19, delete "8one" and insert --8-one--;

In Col. 12, line 20, delete "Hydroxy" and insert --hydroxy--;

In Col. 12, line 25, delete "(+)" and insert --($\pm$)--;

In Col. 12, line 35, delete "methanslfonic" and insert --methanesulfonic--;

UNITED STATES PATENT AND TRADEMARK OFFICE
CERTIFICATE OF CORRECTION

PATENT NO. : 5,489,697
DATED : February 6, 1996
INVENTOR(S) : W.A. Boulanger et al.

It is certified that error appears in the above-indentified patent and that said Letters Patent is hereby corrected as shown below:

In Col. 12, line 40, delete "10propyl" and insert --10-propyl--.

Signed and Sealed this

Third Day of September, 1996

Attest:

BRUCE LEHMAN

Attesting Officer

Commissioner of Patents and Trademarks